(12) United States Patent
Roh (10) Patent No.: US 11,355,248 B2
(45) Date of Patent: Jun. 7, 2022

(54) SYSTEMS AND METHODS OF ASSISTING A USER IN DISCOVERING MEDICAL SERVICES

(71) Applicant: Jeffrey Roh, Seattle, WA (US)

(72) Inventor: Jeffrey Roh, Seattle, WA (US)

(73) Assignee: IX Innovation LLC, Seattle, WA (US)

( * ) Notice: Subject to any disclaimer, the term of this patent is extended or adjusted under 35 U.S.C. 154(b) by 283 days.

(21) Appl. No.: 16/049,751

(22) Filed: Jul. 30, 2018

(65) Prior Publication Data

US 2019/0035508 A1 Jan. 31, 2019

Related U.S. Application Data

(60) Provisional application No. 62/538,051, filed on Jul. 28, 2017.

(51) Int. Cl.
| | |
|---|---|
| *G16H 80/00* | (2018.01) |
| *G16H 10/60* | (2018.01) |
| *G06F 21/32* | (2013.01) |
| *G16H 40/20* | (2018.01) |
| *H04W 4/02* | (2018.01) |
| *G16H 10/65* | (2018.01) |
| *G16H 40/67* | (2018.01) |
| *G16H 40/63* | (2018.01) |

(52) U.S. Cl.
CPC .............. *G16H 80/00* (2018.01); *G06F 21/32* (2013.01); *G16H 10/60* (2018.01); *G16H 10/65* (2018.01); *G16H 40/20* (2018.01); *G16H 40/63* (2018.01); *G16H 40/67* (2018.01); *H04W 4/025* (2013.01); *G06F 2221/2111* (2013.01)

(58) Field of Classification Search
CPC ........ G16H 80/00; G16H 40/20; G16H 10/60; G06F 21/32; H04W 4/025
See application file for complete search history.

(56) References Cited

U.S. PATENT DOCUMENTS

| | | | | |
|---|---|---|---|---|
| 9,928,379 | B1 * | 3/2018 | Hoffer | G16H 40/67 |
| 10,311,388 | B2 * | 6/2019 | Olsen | G16H 10/20 |
| 2002/0010679 | A1 * | 1/2002 | Felsher | G06Q 20/3674 |
| | | | | 705/51 |
| 2012/0166218 | A1 * | 6/2012 | Reiner | G16H 10/20 |
| | | | | 705/2 |
| 2013/0183399 | A1 * | 7/2013 | Blow | A23L 33/16 |
| | | | | 426/2 |

(Continued)

*Primary Examiner* — Michael Tomaszewski
*Assistant Examiner* — Jay M. Patel
(74) *Attorney, Agent, or Firm* — Perkins Coie LLP (57) ABSTRACT

Systems and methods for assisting a user in discovering nearby medical services are disclosed. A method includes identifying a user based on matching of at least one unique identity or biometric details of the user with data stored in a database. Details of an event data may be received from the user. A current geographical location of the user may be determined. Relevant support network data may be identified based on the event data and the current geographical location of the user. The support network data may include data related to pharmacies, doctors, hospitals, clinics, third parties, insurance, and payment agents. Thereafter, the relevant support network data may be presented to the user in form of an event map. The event map may include details related to the event data and the user preferences.

24 Claims, 5 Drawing Sheets

(56) References Cited

U.S. PATENT DOCUMENTS

| | | | | |
|---|---|---|---|---|
| 2013/0285855 A1* | 10/2013 | Dupray | ................ | G01S 5/0278 |
| | | | | 342/451 |
| 2014/0114675 A1* | 4/2014 | Soon-Shiong | ......... | G16H 10/60 |
| | | | | 705/2 |
| 2014/0207486 A1* | 7/2014 | Carty | .................... | G06Q 10/10 |
| | | | | 705/2 |
| 2014/0257047 A1* | 9/2014 | Sillay | ................... | A61B 5/4082 |
| | | | | 600/301 |
| 2014/0278229 A1* | 9/2014 | Hong | .................... | A61B 5/486 |
| | | | | 702/160 |
| 2014/0368601 A1* | 12/2014 | deCharms | ............... | H04L 67/26 |
| | | | | 348/14.02 |
| 2015/0094914 A1* | 4/2015 | Abreu | ................ | B60H 1/00742 |
| | | | | 701/41 |
| 2015/0335288 A1* | 11/2015 | Toth | .................... | A61B 5/6833 |
| | | | | 600/373 |
| 2016/0080548 A1* | 3/2016 | Erickson | ........... | H04M 1/72409 |
| | | | | 455/556.1 |
| 2017/0220998 A1* | 8/2017 | Horn | ...................... | G06Q 50/01 |

\* cited by examiner

SYSTEMS AND METHODS OF ASSISTING A USER IN DISCOVERING MEDICAL SERVICES

CROSS-REFERENCE TO RELATED APPLICATION

This application claims priority to U.S. Provisional Application No. 62/538,051, filed Jul. 28, 2017 which is hereby incorporated by reference in its entirety.

FIELD OF THE DISCLOSURE

The present disclosure is generally related to providing medical assistance to a user, and more particularly related to providing assistance in discovering nearby medical services.

BACKGROUND

Individuals of each country may have varied health care facilities available around them. The individuals use such facilities while medical assistance is required. The individuals may face challenges in seeking such medical assistance while they travel to different countries. An international health insurance can provide certain help in guiding and funding the individuals to health care facilities available in different countries.

Many of these individuals are not accustomed with long wait times, poor access to medical care, few options for immediate response to health concerns, taxed health services, and more. Further, an individual may not expect to have uncertainty in his life especially when it comes to proper and immediate healthcare. A medical condition of the individual may require specialized medical professionals and medical services.

Thus, there is a need for a system that can automatically integrate all the variables, for assisting an individual in conveniently accessing the nearby medical services.

OVERVIEW OF TECHNOLOGY

The present disclosure provides systems and related methods for assisting a user in discovering medical services. In some embodiments, the systems disclosed herein are configured to identify relevant medical service providers based on user-specific information and whether the user has experienced a medical event that may require emergency, urgent, or non-urgent medical services. In one aspect, a method of providing assistance to a user in discovering medical services is provided. The method can include providing one or more databases storing user data and support network data. The user data can include one or more of user personal data, user medical data, and user preference data. The user can be identified based on at least one of a unique identity code or biometric details. The method can further include receiving event data provided by the user and determining a geographical location of the user. Relevant support network data can be identified based on the event data and the geographical location of the user. The relevant support network data can be presented for viewing by the user.

In another aspect, a method of discovering medical services is provided. The method can include receiving user identifier data and event data provided by a user. A user can be identified based on the user identifier data and reference user data associated with the user. The method can further include receiving geographical location data associated with the user. Relevant support network data can be identified based on the event data and the geographical location data. The relevant support network data can be transmitted for viewing by the user. In some embodiments, the relevant support network data can be configured to be displayed on a map with at least one of the event data or the user preference data.

In another aspect, a system for providing assistance to a user in discovering medical services is provided. The system can include one or more databases storing user details and support network data. The user details can include user personal data, user medical data, and user preference data, and the support network data can include data of individuals and agencies providing medical support. The system can further include one or more processors, and memory. The memory can comprise instructions that, when executed by the one or more processors, cause the system to identify the user based on matching of at least one of a unique identity code and biometric details with the user details. The system can receive event data provided by the user and obtain geographical location data associated with the user. Relevant support network data can be identified based on the event data and the geographical location data. The system can provide relevant support network data to the user.

In another aspect, a non-transitory computer-readable storage medium is provided. The non-transitory computer-readable medium can store instructions that, when executed by a computing system, cause the computing system to perform a method for discovering nearby medical services or medical services within a designated area or region. The method can include receiving user details and support network data. The user details can include user personal data, user medical data, and user preference data, and the support network data can include data of individuals and agencies providing medical support. The user can be identified based on matching of at least one of a unique identity code and biometric details with the user details. The method can further include receiving event data provided by the user and receiving a geographical location of the user. Relevant support network data can be identified based on the event data and the geographical location of the user. The relevant support network data can be provided to the user as a map overlaid with at least one of the event data and the user preference data.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

DETAILED DESCRIPTION

The present disclosure provides systems and related methods for assisting a user in discovering nearby medical services. In some embodiments, the systems disclosed herein are configured to identify relevant medical service providers based on user-specific information (e.g., user identity, geographical location, user preferences) and event data (e.g., data indicating that the user has experienced a medical event that may require emergency, urgent, or non-urgent medical services). For example, the system can automatically determine a set of medical service providers customized to the user's particular location, preferences, and medical condition, and visually present that set to the user in an easily understandable format, such as an overlay map on the user's smart phone. The embodiments disclosed herein can advantageously assist users in rapidly finding medical services that are convenient, accessible, and suitable for their specific medical preferences and needs, particularly in situations where the user is unfamiliar with the geographical area or uncertain of the availability of medical services.

Thus, in one aspect, a method of providing assistance to a user in discovering nearby medical services is provided. The method can include providing one or more databases storing user details and support network data. The user details can include user personal data, user medical data, and user preference data, and the support network data can include data of individuals and agencies providing medical support. The user can be identified based on matching of at least one of a unique identity code or biometric details with the user details. The method can further include receiving event data provided by the user and determining a current geographical location of the user. Relevant support network data can be identified based on the event data and the current geographical location of the user. The relevant support network data can be presented to the user as a map overlaid with at least one of the event data and the user preference data.

In another aspect, a method of providing assistance to a user in discovering medical services is provided. The method can include receiving user identifier data and event data provided by a user. The user identifier data can include at least one of a unique identity code or user biometric data. A user can be identified based on the user identifier data and reference user data associated with the user. The method can further include receiving geographical location data associated with the user. Relevant support network data can be identified based on the event data and the geographical location data. The relevant support network data can be transmitted for viewing by the user. The relevant support network data can be configured to be displayed on a map with at least one of the event data or the user preference data.

In another aspect, a system for providing assistance to a user in discovering nearby medical services is provided. The system can include one or more databases storing user details and support network data. The user details can include user personal data, user medical data, and user preference data, and the support network data can include data of individuals and agencies providing medical support. The system can further include one or more processors, and memory. The memory can comprise instructions that, when executed by the one or more processors, cause the system to identify the user based on matching of at least one of a unique identity code and biometric details with the user details. The system can receive event data provided by the user and obtain geographical location data associated with the user. Relevant support network data can be identified based on the event data and the geographical location data. The system can provide relevant support network data to the user. The relevant support network data can be presented as a map overlaid with at least one of the event data and the user preference data.

In another aspect, a non-transitory computer-readable storage medium is provided. The non-transitory computer-readable medium can store instructions that, when executed by a computing system, cause the computing system to perform a method for providing assistance to a user in discovering nearby medical services. The method can include receiving user details and support network data. The user details can include user personal data, user medical data, and user preference data, and the support network data can include data of individuals and agencies providing medical support. The user can be identified based on matching of at least one of a unique identity code and biometric details with the user details. The method can further include receiving event data provided by the user and receiving a current geographical location of the user. Relevant support network data can be identified based on the event data and the current geographical location of the user. The relevant support network data can be provided to the user as a map overlaid with at least one of the event data and the user preference data.

In another aspect, a method of providing assistance to a user in discovering medical services is provided. The method can include transmitting user identifier data and event data provided by a user. The user identifier data can include at least one of a unique identity code or user biometric data for identifying a user. The method can further include providing geographical location data associated with the user to a remote server configured to identify a relevant support network data based on the event data and the geographical location data. Relevant support network data can be received from the remote server for viewing by the user. The relevant support network data can be displayed to indicate at least one of the event data or the user preference data.

Some embodiments of this disclosure, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present disclosure, the preferred, systems and methods are now described.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

Figure 1:
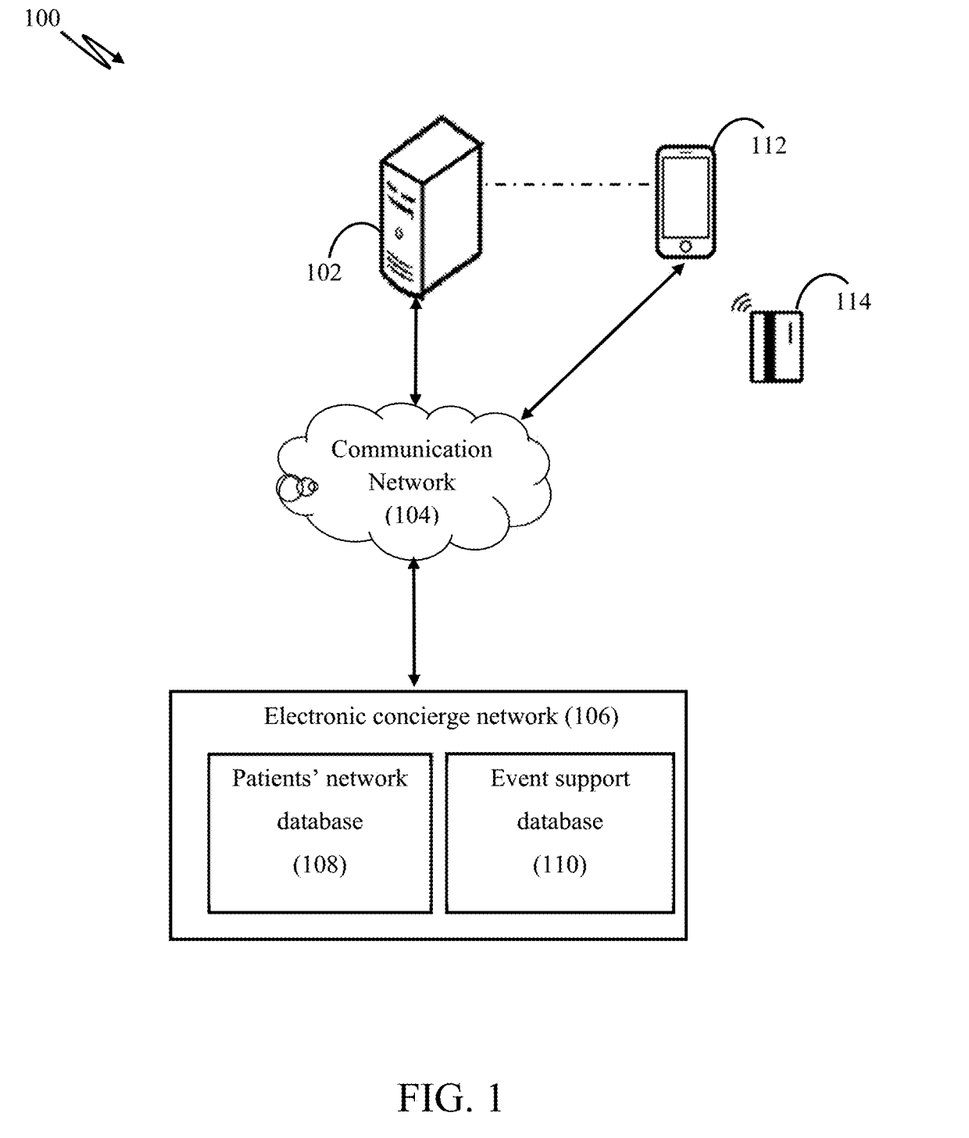
FIG. 1 illustrates a network connection diagram 100 of a system 102 for assisting a user in discovering nearby medical services, according to an embodiment.

FIG. 1 illustrates a network connection diagram 100 of a system 102 for providing assistance to a user in discovering nearby medical services, according to an embodiment. The system 102 may be connected with a communication network 104. The communication network 104 may further be connected with an electronic concierge network 106 for allowing data transfer between the system 102 and the electronic concierge network 106. Optionally, the communication network 104 may further be connected with a user device 112 for allowing data transfer between the user device 112, the system 102, and/or the electronic concierge network 106.

The system 102 may be a computing system or device including hardware and software components configured to implement the various methods described herein. For example, the system 102 can be a computer, such as laptop or desktop computer. In some embodiments, the system 102 is or includes a server, such as a cloud server implemented across any suitable combination of hardware and/or virtual computing resources.

The communication network 104 may be a wired and/or a wireless network. The communication network 104, if wireless, may be implemented using communication techniques such as Visible Light Communication (VLC), Worldwide Interoperability for Microwave Access (WiMAX), Long Term Evolution (LTE™), Wireless Local Area Network (WLAN), Infrared (IR) communication, Public Switched Telephone Network (PSTN), Radio waves, and other communication techniques known in the art.

In one embodiment, the electronic concierge network 106 may be implemented as a facility over a cloud network and may include a group of modules. The group of modules may include a patients' network database 108, and an event support database 110. The patients' network database 108 may be configured to store user data into a database, such as user personal data, user medical data, and/or user preference data. The stored data can include, without limitation, patient records, medical data (e.g., medical history, familial medical history, allergies, medications), billing information, insurance information, employer information, preference data (e.g., preferred doctors and/or facilities), travel itinerary, or the like. The event support database 110 may be configured to store support network data and to determine a support network for a user. The support network may include persons and places that provide medical services, such as pharmacies, doctors, hospitals, clinics, third parties, insurance, and/or payment agents. The event support database 110 may store a user Identity (ID) of the user, biometric data, and/or authentication data and may store the data along with a current geographical location of the user.

The user device 112 may be any device having suitable software and hardware components for receiving input data from a user and displaying output data to the user. In one embodiment, relevant information may be displayed on a Graphical User Interface (GUI) of the user device 112. A smart phone is shown as the user device 112 in FIG. 1, as an example. Further, the user device 112 may be any other device including a GUI, for example, a laptop, desktop, tablet, phablet, mobile device, or other such devices known in the art. The user device 112 may include a local software application (e.g., a desktop application, web application, or mobile application) configured to implement the various methods described herein. The user device 112 may be configured to communicate directly with the system 102, or indirectly via the communication network 104.

Although FIG. 1 illustrates an exemplary configuration for the systems of the present disclosure, alternative configurations may also be used. For example, although FIG. 1 depicts the user device 112 and system 102 as separate devices, in alternative embodiments, the user device 112 may include the system 102, or one or more components thereof (e.g., one or more of the modules discussed in connection with FIG. 2). Accordingly, some or all of the functionality described herein with respect to the system 102 may also be performed by the user device 112, and vice-versa. Similarly, although FIG. 1 depicts the system 102 and the electronic concierge network 106 as separate elements, in alternative embodiments, the system 102 may include the electronic concierge network 106, or one or more components thereof (e.g., the patients' network database 108 and/or the event support database 110). Accordingly, some or all of the functionality described herein with respect to the system 102 may also be performed by the electronic concierge network 106, and vice-versa.

Figure 2:
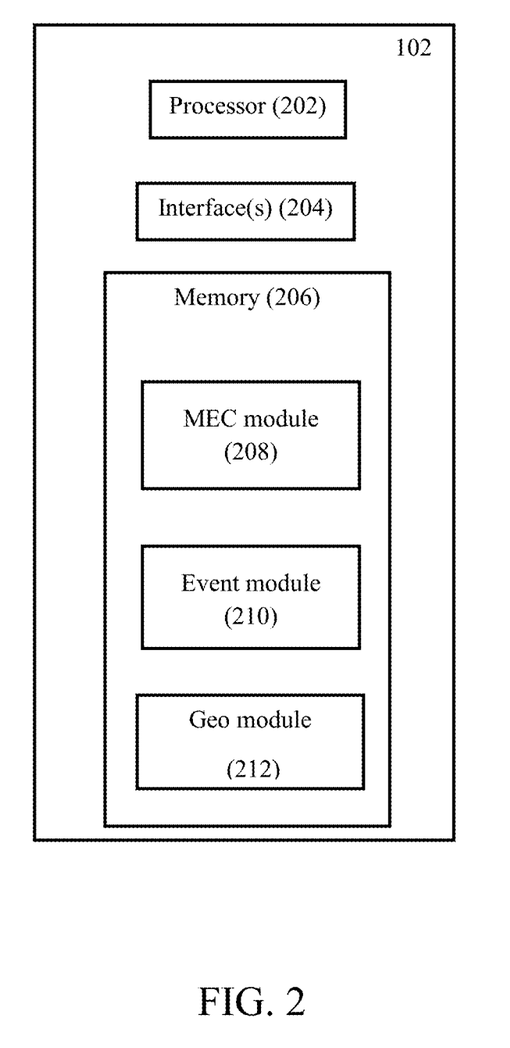
FIG. 2 illustrates a block diagram showing different components of the system 102, according to an embodiment.

In one embodiment, referring to FIG. 2, a block diagram showing different components of the system 102 is explained. The system 102 includes a processor 202, interface(s) 204, and the memory 206. The processor 202 may execute an algorithm stored in the memory 206 providing real-time assistance to the user in discovering nearby medical services. The processor 202 may also be configured to decode and execute any instructions received from one or more other electronic devices or server(s).

In one embodiment, the processor 202 may include one or more general purpose processors (e.g., INTEL® or Advanced Micro Devices® (AMD) microprocessors) and/or one or more special purpose processors (e.g., digital signal processors or Xilinx® System On Chip (SOC) Field Programmable Gate Array (FPGA) processor). The processor 202 may be configured to execute one or more computer-readable program instructions, such as program instructions to carry out any of the functions described in this description.

The interface(s) 204 may help the user to interact with the system 102. The interface(s) 204 of the system 102 may either accept an input from the user or provide an output to the user, or may perform both the actions. The interface(s) 204 may either be a Command Line Interface (CLI), Graphical User Interface (GUI), or a voice interface.

The memory 206 may include, but is not limited to, fixed (hard) drives, magnetic tape, floppy diskettes, optical disks, Compact Disc Read-Only Memories (CD-ROMs), and magneto-optical disks, semiconductor memories, such as ROMs, Random Access Memories (RAMs), Programmable Read-Only Memories (PROMs), Erasable PROMs (EPROMs), Electrically Erasable PROMs (EEPROMs), flash memory, magnetic or optical cards, or other type of media/machine-readable medium suitable for storing electronic instructions.

The memory 206 may include modules, implemented as programmed instructions executed by the processor 202. In one case, the memory 206 may include a Mobile Electronic Concierge (MEC) module 208, an event module 210, and a geo module 212. The memory 206 can be non-transitory computer-readable storage medium storing instructions that, when executed by a computing system, cause the computing system to perform methods disclosed herein.

Figure 3:
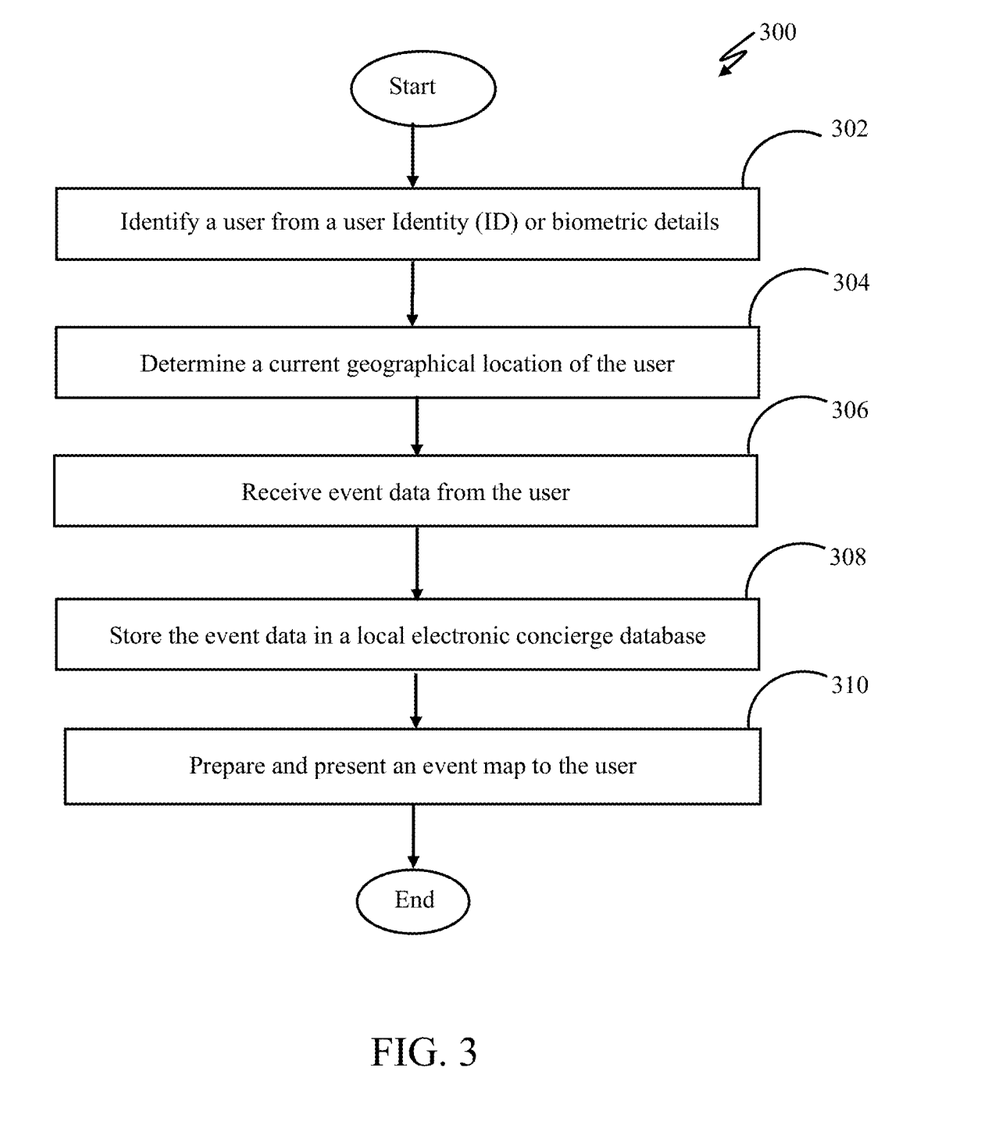
FIG. 3 illustrates a flow chart 300 showing a method executed by a Mobile Electronic Concierge (MEC) module 208 and an event module 210 of the system 102, according to an embodiment.

Functioning of the MEC module 208 and the event module 210 will now be explained with reference to a flowchart 300 shown in FIG. 3, according to an embodiment. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

At first, the user may be identified by the system 102, at step 302. In one case, the user may be identified based on user identifier data provided by the user. For example, the user may input user identifier data into the user device 112, and the user device 112 may transmit the user identifier data to the system 102. User identifier data may include a user Identity (ID), biometric details (e.g., user biometric data), and/or authentication details (e.g., user authentication data). The user ID may be stored in or may be presented using the user's credit cards, debit cards, key fobs, smart cards, electronic ID access cards, and the like. In one case, a Near Field Communication (NFC) card 114 may be used to prove the user ID. The user ID may be determined by a scanner present on the user device 112.

In one embodiment, the biometric details of the user may be provided in form of fingerprints, iris scans, unique identification marks on user's body, and the like. The biometric details of the user may be verified by a fingerprint scanner, an iris scanner, or a suitable hardware present on the user device 112. A smart phone is shown as the user device 112 in FIG. 1, as an example. As mentioned previously, the user device 112 may be any other device such as a laptop, a desktop, a tablet, a phablet, or other such devices known in the art. In one embodiment, the authentication details may include credentials, passwords, login identifiers, usernames, security tokens, or the like. The authentication details may be used for two-factor or multifactor identification.

In some embodiments, the user is identified based on matching of at least one of a unique identity code or biometric details with reference user data, also referred to herein as user details. In one embodiment, the user is identified based on both a unique identity code and biometric details. For example, the system 102 may receive the unique identity code and/or biometric details from the user, and can compare the unique identity code and/or biometric details with previously stored user data or details (e.g., user details previously stored in one or more databases of the electronic concierge network 106) or reference user data. If the unique identity code and/or biometric details match the stored user details, the user is successfully identified, and the system 102 can proceed to step 304.

Post successful identification of the user, a current geographical location of the user may be determined, at step 304. In one case, the current geographical location of the user may be determined by a geographical location sensing device, such as the geo module 212. The geo module 212 may determine the current geographical location based on cellular tower data (e.g., via cell tower triangulation), satellite data, local network data, or the like. In another case, a Global Positioning Device (GPS) present in the system 102 or user device 112 may be used for determining the current geographical location of the user. In some embodiments, the user device 112 may determine the current geographical location of the user, and transmit the current geographical location to the system 102.

In some embodiments, step 304 includes determining a predicted future geographical location of the user, as an alternative to or in addition to determining the current geographical location of the user. The predicted future geographical location can be determined in a variety of ways. For example, the user may input a travel itinerary data (e.g., via the user device 112) including times and locations of travel. The user may input a particular time at which medical services are desired (e.g., a future date for refilling a prescription). The user device 112 and/or system 102 can compare the input time with the travel itinerary data to determine the predicted future geographical location of the user during that time.

Post determining the current and/or predicted future geographical location, event data may be received from the user, at step 306. In some embodiments, the event data includes data indicative of a medical event. The medical event may be an event related to the user's past and/or current health, such as a medical emergency (e.g., heart attack, severe injury, fainting, allergic reactions) or a medical non-emergency (e.g., cold or flu symptoms, fever, headache, minor injury). The medical event may be an event that the user wishes to schedule or perform at a particular time, such as an appointment with a medical service provider or picking up medication.

The user may input event data into the user device 112, and the user device 112 may transmit the event data to the system 102. Alternatively or in combination, the event data may be generated automatically by the user device 112 and transmitted to the system 102. For example, the user device 112 may automatically detect when a medical event has occurred (e.g., based on time, location, health information received via a smart watch or health monitoring device) and automatically transmit event data to the system 102. In some embodiments, the user device 112 can include or be in communication a wearable device, such as a wearable smart watch or glucose sensor, that detects one or more events (e.g., an irregular heart rate, abnormal blood pressure, etc.).

The event data may be received in the form of, but not limited to, a text string, or an audio request, or an audio request reduced to a text string, or an image. For example, the user input can include an image of a wound, audio (e.g., audio of a user requesting services), and/or text describing the services requested. Further, the event data may include a set of questions to be answered by the user (e.g., questions regarding the type, timing, and/or severity of symptoms), and/or the user's responses thereto. The event data can be answers to one or more questions for determining user health, condition information, pain information, allergy information, and priority information. The priority information can be used to determine whether the user requires immediate assistance, urgent care, or the like. If the event module 210 (FIG. 2) determines that the user requires immediate attention, medical assistance can be sent to the user. If the event module 210 (FIG. 2) determines that urgent care should be provided, the event module 210 can identify at least one available urgent care facility. The Mobile Electronic Concierge (MEC) module 208 can receive and store the event data from the user and/or event module 210.

In some embodiments, step 306 includes receiving user preference data. The user preference data may include, but is not limited to, non-medical data that includes, without limitation, transportation information, hotel information, purchasing data (e.g., shopping preferences), restaurant data, airport data, or the like. The user preference data may also include, without limitation, medical data that includes, without limitation, preferred type of medical center (e.g., hospital, urgent care center, etc.), preferred service capabilities (e.g., surgical facilities with blood bank), preferred rating (e.g., facilities with suitable ratings such as hospitals with ratings at or above a user selected level, or minimum doctor ratings), preferred training and/or education level of service providers, preferred visit times, price preferences, payment preferences (e.g., insurance or cash-based), preferred insurance coverage (e.g., whether services will be in network or out of network), or the like.

The user may input the user preference data into the user device 112, and the user device 112 may transmit the user preference data to the system 102. In some embodiments, the user preference data is stored in a database (e.g., the patients' network database 108 of FIG. 1), and the system 102 retrieves the user preference data directly from the database based on the user identification.

The event data may be stored in a local electronic concierge database, at step 308. For example, the event data may be stored by the event support database 110 of FIG. 1. Optionally, the user preference data may also be stored in a local electronic concierge database, such as the patients' network database 108 of FIG. 1.

Figure 4:
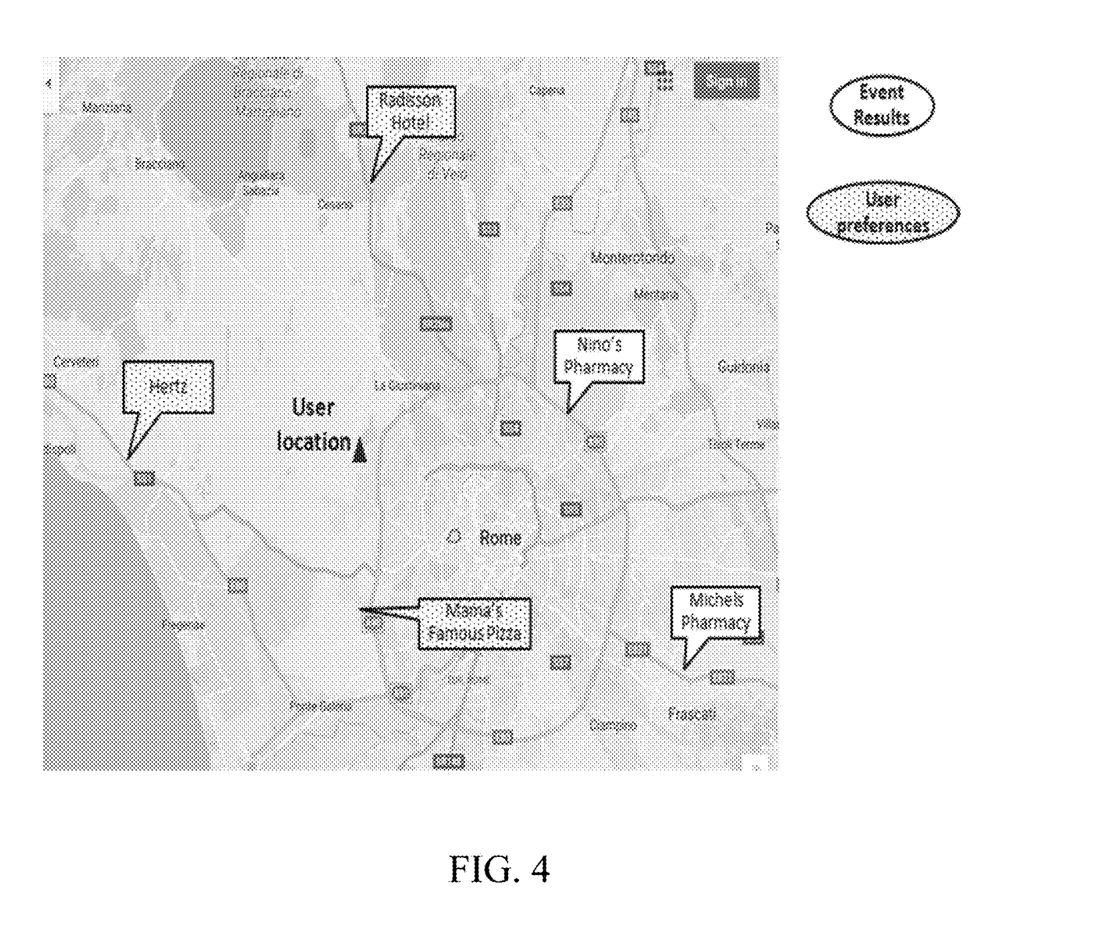
FIG. 4 illustrates an overlay map including event data and user preference data, according to an embodiment.

In an embodiment, an event map may be prepared and presented to the user, at step 310. The event map may be displayed to the user via a graphical user interface of the user device 112. In one case, the event map may be presented as a map overlaid with the event data and/or the user preference data, as illustrated in FIG. 4. Further, the event data and/or the user preference data filtered and shown based on the current geographical location of the user, may be identified as relevant support network data. The relevant support network data may include locations and information related to medical service providers, such as pharmacies, doctors, hospitals, clinics, third parties, insurance, payment agents, and the like. Such locations and information may be filtered based on the current geographical location of the user and may be presented to the user in form of the relevant support network data. For example, locations may be excluded based on estimated travel time, traffic conditions, availability of transportation (e.g., buses, trains, etc.), or the like. The user can adjust the filter settings.

Figure 5:
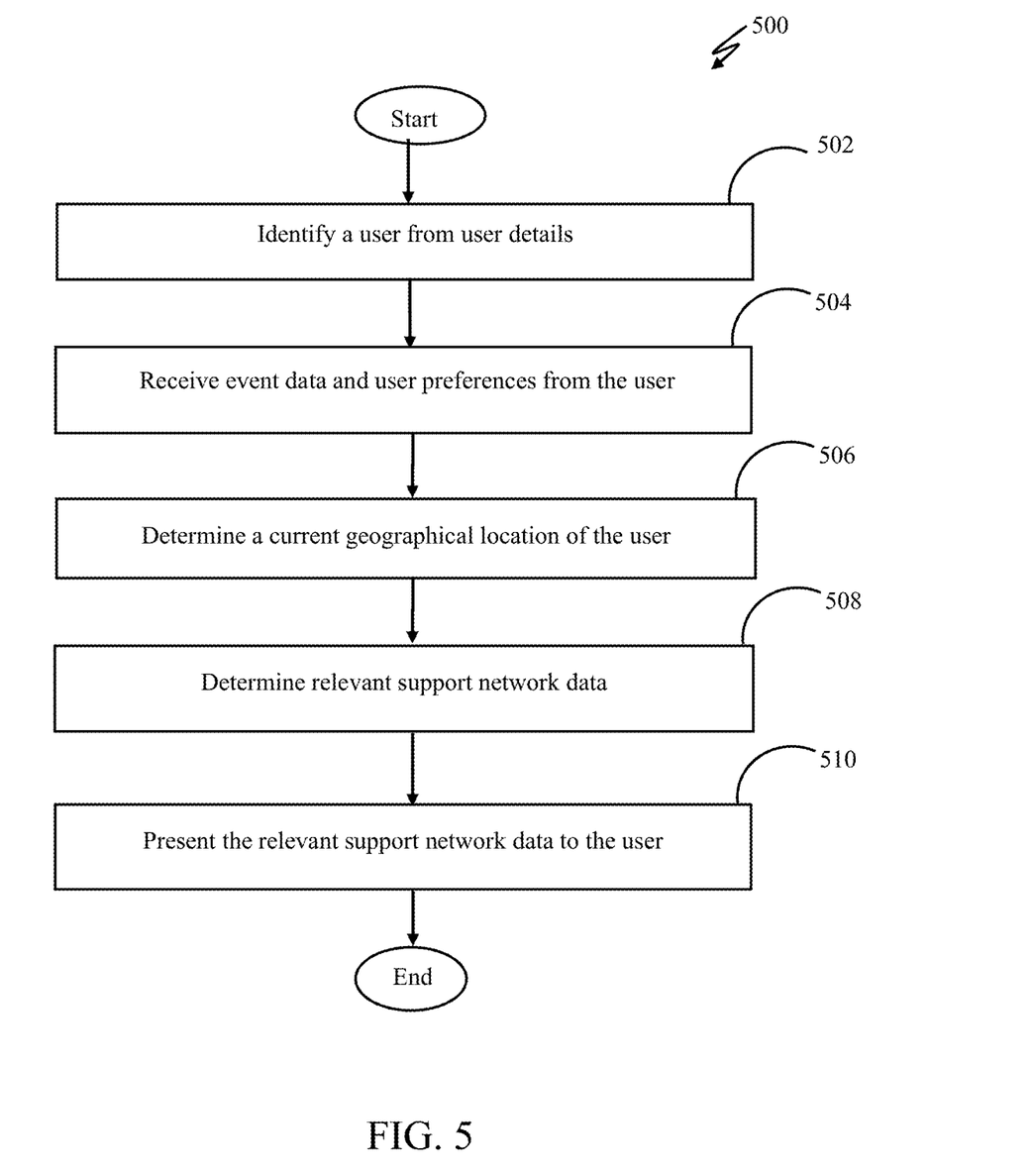
FIG. 5 illustrates a flowchart 500 showing a method for assisting the user in discovering nearby medical services, according to an embodiment.

FIG. 5 illustrates a flowchart 500 showing a method of assisting a user in discovering nearby medical services, according to an embodiment. The flowchart 500 is explained in conjunction with the elements disclosed in the above explained Figures. For example, one or more steps of the flowchart 500 can be performed by the system 102 (e.g., the MEC module 208, event module 210, and/or geo module 212), user device 112, or combinations thereof. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The flowchart 500 of FIG. 5 shows the architecture, functionality, and operation for assisting a user in discovering nearby medical services. Any process descriptions or blocks in flowcharts should be understood as representing modules, segments, or portions of code which include one or more executable instructions for implementing specific logical functions or steps in the process, and alternate implementations are included within the scope of the example embodiments in which functions may be executed out of order from that shown or discussed, including substantially concurrently or in reverse order, depending on the functionality involved. In addition, the process descriptions or blocks in flow charts should be understood as representing decisions made by a hardware structure such as a state machine. The flowchart 500 starts at the step 502 and proceeds to step 510.

At step 502, a user may be identified by the system 102, as described with respect to step 302 of flowchart 300.

At step 504, event data and/or user preferences may be received from the user, as described with respect to step 306 of flowchart 300.

At step 506, a current geographical location of the user may be determined, as described with respect to step 304 of flowchart 300. Alternatively or in combination, a predicted future geographical location of the user may be determined, as described with respect to step 304 of flow chart 300.

At step 508, relevant support network data may be identified based on the event data, user preference data, and/or the current and/or predicted future geographical location of the user. The relevant support network data may include locations and information related to medical service providers, such as pharmacies, doctors, hospitals, clinics, third parties, insurance, payment agents, and the like. In some embodiments, the system 102 uses the event data, user preference data, and/or the current and/or predicted future geographical location of the user to automatically identify a subset of medical service providers (e.g., a subset of the providers from the support network data stored in event support database 110 of FIG. 1) that are relevant to the user's particular situation (e.g., are suitable for responding to the user's event, fulfill some or all of the user's preferences, and/or are located close to the user's current or predicted future geographical location).

For example, in one embodiment, the event module can evaluate the event data to determine that the user has, for example, a time-critical emergency that may require surgery. The MEC module can determine a relevant support network data that includes a nearby hospital that provides surgical services. In another case, the event module may evaluate the event data and determine that the user has non-urgent infection. The MEC module and/or concierge network can then determine a relevant support network data that includes a clinic and a pharmacy. The user can select a recommended pharmacy near a hotel, place or work, or home to conveniently purchase medication. If the user is travelling, the MEC module and/or concierge network can identify relevant support network data based on the user's itinerary, which can be retrieved from the user's mobile device (e.g., device 112) or inputted by the user. For example, if the user is travelling to another city, the relevant support network data can include a pharmacy near the user's hotel in that city. The relevant support network data can therefore provide a medical services plan for the user's trip. In another embodiment, the relevant support network data can include different sets of relevant support network data. For example, a first set of relevant support network data for discovering medical services near a user's residence and a second set of relevant support network data for discovering medical services near the user's place of work. The relevant support network data can include information about the services, such as hours of operation, ratings, directions to/from medical facilities.

At step 510, the relevant support network data may be presented to the user. In some embodiments, the relevant support network data may be displayed on a graphical user interface of the user device 112. For example, the relevant support network data may be presented as a map overlaid with the event data and/or the user preference data, as described in step 310 of flowchart 300.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be affected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

Embodiments disclosed herein are discussed primarily with respect to providing assistance for discovering medical services. However, it shall be appreciated that the embodiments disclosed herein can also be used to discover other types of services, such as dental or vision services. The embodiments disclosed herein can be applied to any healthcare-related services and service providers, including but not limited to doctors, nurse practitioners, surgeons, cosmetic surgeons, dentists, orthodontists, periodontists, cosmetic dentists, optometrists, pharmacists, psychotherapists, behavioral therapists, physical therapists, massage therapists, chiropractors, and the like.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A method of providing assistance to a personal mobile device user in obtaining medical services, the method comprising:

providing one or more databases storing user details and support network data, wherein the user details comprise user personal data, patient records, user and family medical history, allergies, medications, and/or user insurance data, and wherein the support network data comprises data of individuals and agencies providing medical support and service capabilities;

identifying the user based on matching of at least one of a unique identity code or biometric details with the user details;

communicating event data associated with the user, wherein the event data indicates a medical event that requires a medical recourse;

determining a current geographical location of the user based on information received from a geographical location sensing circuit;

predicting a future geographical location for the user according to a travel itinerary data, wherein the future geographical location corresponds to a non-residential area for the user;

identifying relevant support network data based on comparing the event data, the user details, and the current and future geographical locations of the user, wherein the relevant support network data at least partially represents a set of medical service providers that (1) have service capabilities suitable for responding to the medical event and (2) satisfy real-time restrictions on estimated travel time and transportation availability associated with the current and future geographical locations, wherein the real-time restrictions correspond to the medical recourse; and presenting the relevant support network data through the personal mobile device, wherein the relevant support network data is presented overlaid on a map with at least one of the event data and the user preference data.

2. The method of claim 1, wherein the unique identity code is stored in an electronic Identity (ID) access card.

3. A method of providing assistance to a user of a mobile device in obtaining medical services, the method comprising:

receiving user identifier data and event data provided by the user, wherein the user identifier data includes at least one of a unique identity code or user biometric data;

identifying the user based on the user identifier data and reference user data associated with the user;

receiving, via a network interface, geographical location data associated with the user and representative of information determined by a geographical location sensing circuit;

estimating a future location for the user according to user schedule data;

identifying relevant support network data based on the event data, the estimated future location, and the geographical location data, wherein the relevant support network data represents a set of medical service providers that satisfy real-time restrictions on estimated travel time and transportation availability associated with the current and future geographical locations; and presenting the relevant support network data through the mobile device, wherein the relevant support network data is configured to be displayed on a map with at least one of the event data or the user preference data.

4. The method of claim 3, further comprising receiving user data and support network data, wherein the user data comprises user personal data, user medical data, and user preference data, and wherein the support network data comprises data of medical service providers.

5. The method of claim 3, wherein the relevant support network data is configured to be overlaid on the map.

6. The method of claim 3, wherein the at least one of the unique identity code or the user biometric data is received from a smart phone, a laptop, a tablet, or a phablet.

7. The method of claim 3, wherein the event data comprises data related to the user's current health and/or geographical locations associated with the user, and wherein the geographical location data include current geographical location data and/or predicted future geographical location data.

8. The method of claim 3, wherein the event data comprises at least one of a text string, an audio request, an audio request reduced to a text string, or an image.

9. The method of claim 3, wherein the relevant support network data comprises locations and information related to one or more pharmacies, doctors, hospitals, clinics, third parties, insurance agents, or payment agents.

10. The method of claim 9, further comprising filtering the locations and information based on the current geographical location of the user.

11. A system for providing assistance to a user of a personal device in obtaining medical services, the system comprising:

one or more databases storing user details and support network data, wherein the user details comprise user personal data, patient records, user and family medical history, allergies, medications, and/or user insurance data, and wherein the support network data comprises data of individuals and agencies providing medical support and service capabilities;

a network interface configured to obtain geographical location data associated with the user, wherein the geographical location data represents a current location of the user as determined by a geographical location sensing circuit;

one or more processors; and memory comprising instructions that, when executed by the one or more processors, cause the system to:

identify the user based on matching of at least one of a unique identity code and biometric details with the user details, receive event data associated with the user, wherein the event data indicates a medical event that requires a medical recourse, predicting a future geographical location for the user according to a user schedule data;

identify relevant support network data based on comparing the event data, the user details, the future geographical location, and the geographical location data, wherein the relevant support network data at least partially represents a set of medical service providers that (1) have service capabilities suitable for responding to the medical event and (2) satisfy real-time restrictions on estimated travel time and transportation availability associated with the current and future geographical locations, wherein the real-time restrictions correspond to the medical recourse, and present the relevant support network data through personal device the user, wherein the relevant support network data is presented through the personal device as at least one of the event data and the user preference data overlaid on a map.

12. The system of claim 11, wherein the instructions cause the system to present the relevant support network data through a smart phone, a laptop, a desktop, a tablet, or a phablet.

13. The system of claim 11, wherein the at least one of the unique identity code and biometric details is received from the personal device.

14. The system of claim 11, further comprising a geographical location sensing device configured to determine the current geographical location of the user.

15. The system of claim 11, further comprising one or more interfaces configured to receive the event data from the user and present the relevant support network data to the user.

16. The system of claim 11, wherein the relevant support network data comprises locations and information related to one or more pharmacies, doctors, hospitals, clinics, third parties, or insurance and payment agents.

17. The system of claim 16, wherein the locations and information are filtered based on the current geographical location of the user.

18. A non-transitory computer-readable storage medium storing instructions that, when executed by a computing system, cause the computing system to perform a method for providing assistance through a personal device to a user in obtaining medical services, comprising:
receiving user details and support network data, wherein the user details comprise user personal data, user medical data, and user preference data, and wherein the support network data comprises data of individuals and agencies providing medical support;
identifying the user based on matching of at least one of a unique identity code and biometric details with the user details;
communicating event data provided by the user;
receiving, via a network interface, a current geographical location of the user determined by a geographical location sensing circuit;
predicting a future geographical location for the user according to user schedule data;
identifying relevant support network data based on the event data, the future geographical location, and the current geographical location of the user, wherein the relevant support network data at least partially represents a set of medical service providers that satisfy real-time geographic restrictions, wherein the geographic restrictions are based on the event data and estimated travel time and/or transportation availability associated with the current and future geographical locations; and
presenting the relevant support network data through the personal device of the user, wherein the relevant support network data is configured for presentation overlaid on a map with at least one of the event data and the user preference data.

19. The non-transitory computer-readable storage medium of claim 18, wherein the at least one of the unique identity code and biometric details is received from a smart phone, a laptop, a desktop, a tablet, or a phablet.

20. The non-transitory computer-readable storage medium of claim 18, wherein the event data comprises data related to the user's current health.

21. The non-transitory computer-readable storage medium of claim 18, wherein the event data comprises a text string, an audio request, an audio request reduced to a text string, or an image.

22. The non-transitory computer-readable storage medium of claim 18, wherein the relevant support network data comprises locations and information related to one or more pharmacies, doctors, hospitals, clinics, third parties, or insurance and payment agents.

23. The non-transitory computer-readable storage medium of claim 22, wherein the method further comprises filtering the locations and information based on the current geographical location of the user.

24. The method of claim 1, wherein:
the event data represents a medical emergency automatically detected based on data from one or more wearable devices and/or one or more continuous health-monitoring devices and related to a past or existing health condition of the user;
the communicated event data represents an image associated with the medical event; and
the identified relevant support network data includes an available urgent care facility.

\* \* \* \* \*